US006292697B1

(12) United States Patent
Roberts

(10) Patent No.: US 6,292,697 B1
(45) Date of Patent: Sep. 18, 2001

(54) TESTING STERILE PACKAGED COMPONENTS OF AN IMPLANTABLE MEDICAL DEVICE PRIOR TO CHRONIC IMPLANTATION

(75) Inventor: Jonathan P. Roberts, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/504,596

(22) Filed: Feb. 15, 2000

(51) Int. Cl.$^7$ .................................................. A61N 1/37
(52) U.S. Cl. ...................................................... 607/27
(58) Field of Search ............................ 607/27; 206/328, 206/438, 210, 701

(56) References Cited

U.S. PATENT DOCUMENTS

| | | | |
|---|---|---|---|
| 4,423,732 | 1/1984 | Tarjan | 128/419 P |
| 4,522,209 | 6/1985 | Patrick | 128/419 R |
| 4,545,381 | 10/1985 | Bournay | 128/419 P |
| 4,605,007 | 8/1986 | Heraly | 128/419 PT |
| 4,705,042 | 11/1987 | Giurtino | 128/419 PT |
| 4,776,350 | 10/1988 | Grossman | 128/799 |
| 4,830,005 | 5/1989 | Woskow | 128/419 PT |
| 5,080,096 | 1/1992 | Hooper | 128/419 R |
| 5,237,991 | 8/1993 | Baker, Jr. | 607/27 |
| 5,402,884 | 4/1995 | Gilman | 206/328 |
| 5,462,157 | 10/1995 | Freeman | 206/210 |
| 5,535,752 | 7/1996 | Halperin | 128/670 |
| 5,564,434 | 10/1996 | Halperin | 128/748 |
| 5,579,919 | 12/1996 | Gilman | 206/701 |
| 5,817,151 | 10/1998 | Olson | 607/142 |
| 5,843,132 | 12/1998 | Ilvento | 607/10 |
| 5,850,920 | 12/1998 | Gilman | 206/701 |
| 5,861,919 | 1/1999 | Sun | 607/60 |
| 5,891,175 | 4/1999 | Walmsley | 607/17 |
| 5,891,180 | 4/1999 | Greeninger | 607/32 |
| 5,919,221 | 7/1999 | Miesel | 607/119 |
| 5,931,861 | 8/1999 | Werner | 607/115 |
| 5,984,102 | 11/1999 | Tay | 206/701 |

*Primary Examiner*—Scott M. Getzow
(74) *Attorney, Agent, or Firm*—Girma Wolde-Michael

(57) ABSTRACT

Apparatus, systems and methods for coupling components of an implantable medical device that are contained within separate sterile packages together and testing operation thereof prior to chronic implantation are disclosed. In particular, testing of the integrity of the lead conductors and other electrical components coupled therewith and the testing and calibration of an implantable sensor, e.g., an implantable pressure sensor, coupled to a programmable, implantable hemodynamic monitor (IHM) or implantable pulse generator (IPG) while in respective sterile packages are disclosed. The lead and IPG/IHM sterile packages are provided with package connectors that couple the terminals of the IPG/IHM and lead to external package connector arrays. The package connector arrays are coupled together, and a programmer is employed to downlink telemetered commands to the IPG or IHM to test the sensor and/or lead conductors and uplink via telemetry the results to the programmer for display. When a lead borne pressure sensor is under test, the uplink telemetered pressure readings are compared to a reference pressure reading. A correction factor is determined if the uplink telemetered and reference pressure readings differ, and the correction factor is downlink telemetered from the programmer into memory of the IPG or IHM for use in adjusting the sensor pressure readings. The pressure test may be conducted both at atmospheric pressure and at elevated pressures correlated to typical systolic blood pressures, and the correction factor may be derived from all tests.

20 Claims, 5 Drawing Sheets

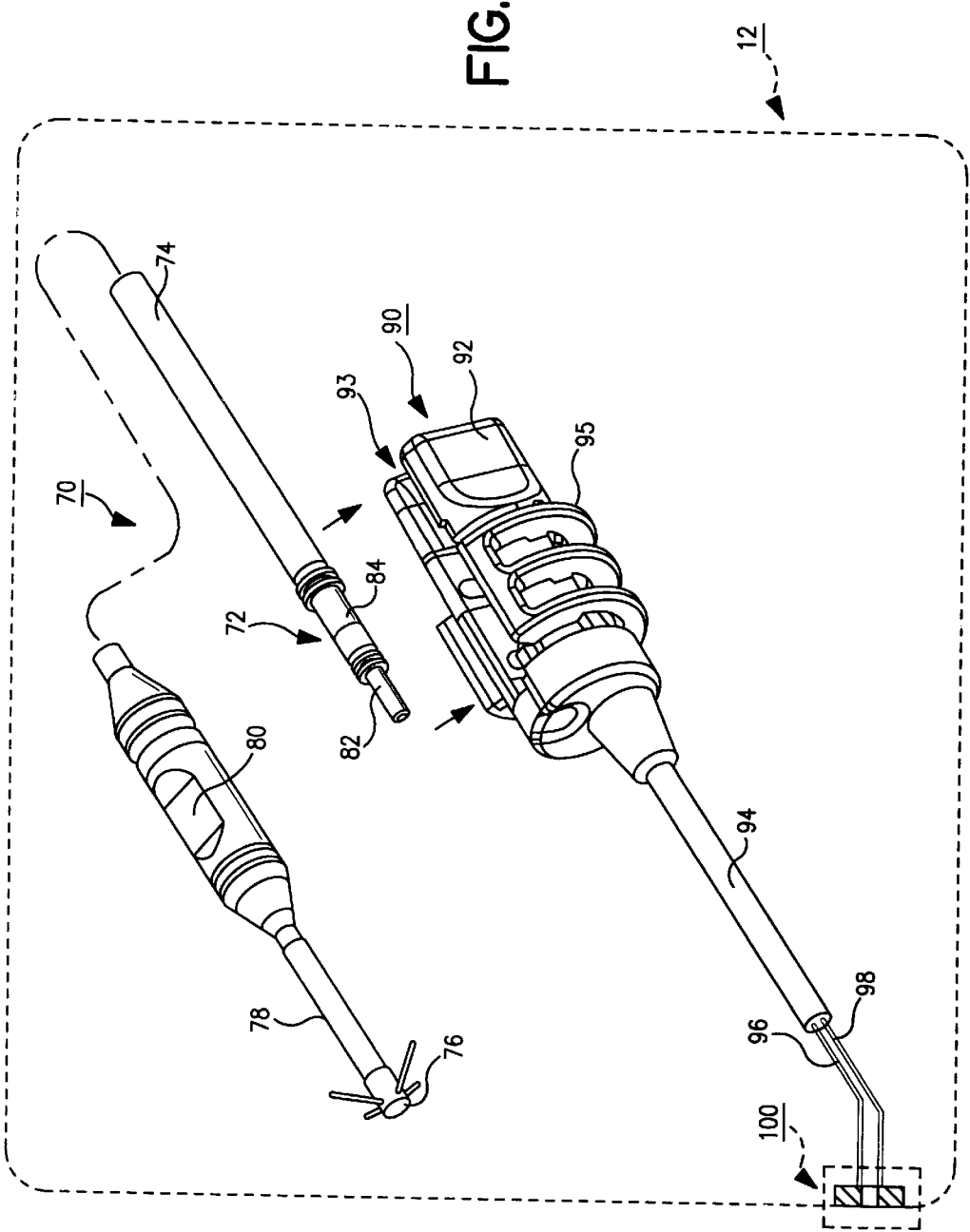

TESTING STERILE PACKAGED COMPONENTS OF AN IMPLANTABLE MEDICAL DEVICE PRIOR TO CHRONIC IMPLANTATION

FIELD OF THE INVENTION

The present invention relates to apparatus, systems and methods for coupling components of an implantable medical device (IMD) that are contained within separate sterile packages together and testing operation thereof prior to chronic implantation, and particularly to calibrating an implantable sensor, e.g., an implantable pressure transducer, coupled to an implantable monitor or pulse generator while in respective sterile packages prior to their implantation in a patient.

BACKGROUND OF THE INVENTION

A number of different IMDs comprise hermetically sealed implantable pulse generators (IPGs) or monitors coupled with implantable leads having electrodes for delivering electrical pulses or shocks to and/or sensing electrical activity of a body organ, muscle or nerve and/or bearing sensors, e.g., blood gas, pH, temperature, and pressure sensors. Certain implantable pacing systems and implantable cardioverter/defibrillators (ICDs) employ pressure sensors to monitor cardiac blood pressure through a capacitive pressure sensor in the distal portion of a lead inserted into a patient's heart. Pacing leads having a pressure sensor are used in such cardiac pacing systems to adjust pacing rate in a rate responsive pacing mode, e.g., the VVIR, DDDR, and DDIR pacing modes. Pressure sensors may likewise be utilized on pacing leads for other purposes, such as determining capture by a delivered pace pulse. The pressure sensor on the pacing lead detects the pressure inside the heart chamber into which the lead is inserted, and converts the detected pressure into electronic information which is transmitted back to the pacemaker. The pacing system then analyzes the information received from the pressure sensor and determines an appropriate rate response or uses the information for another purpose. Pressure sensor bearing leads of this type are disclosed, for example, in commonly assigned U.S. Pat. Nos. 5,535,752 and 5,564,434. Pacing systems utilizing ventricular blood pressure, among other physiologic signals, for determining an appropriate rate response are well known in the art, as shown, for example, in U.S. Pat. No. 5,891,175.

In addition, the CHRONICLE™ Implantable Hemodynamic Monitor (IHM) made by Medtronic, Inc., assignee of this patent application, continuously monitors right ventricular pressure through such a capacitive pressure sensor bearing lead as disclosed in the '752 and '434 patents inserted into a patient's heart for monitoring the cardiac pressure and EGM and storing such data. A number of other sensors have been proposed to monitor body parameters, e.g., blood gas, pH, temperature and the like for obtaining and using or storing particular information. Such sensors require calibration against standards to ensure that they will accurately measure the body parameter of interest.

For example, it is critical to establish the accuracy of the pressure sensor prior to implanting a pacing or sensing lead having a pressure sensor into a patient. The accuracy of the pressure sensor is not guaranteed, or at least should not be relied upon by physicians, simply based upon the manufacturer's packaging and prior testing of the pressure transducer's accuracy. Once implanted into a patient, the pressure sensor accuracy cannot be easily verified.

The accuracy of the pressure sensor can be divided into two parameters, "baseline pressure" and "scale factor." In regard to the former parameter, the pressure detected by the sensor must accurately reflect the true pressure inside the particular chamber into which it is inserted. Thus, the "baseline pressure" value of the sensor must be established relative to a known applied pressure. In regard to the latter parameter, any increase or decrease in pressure reported by the sensor in the chamber of the heart into which it has been inserted must accurately reflect the amount of pressure actually increased or decreased. Thus, an accurate "scale factor" for the sensor must be established, in order to have complete calibration. In addition, it is preferable that such parameters be adjusted within a sterile environment.

Commonly assigned U.S. Pat. No. 5,919,221 discloses a method and apparatus for testing and calibrating a pressure transducer of the type described in the above-referenced '752 and '434 patents. A calibration vessel is provided having a housing forming a vessel reservoir which, in use, contains the distal portion of the pacing lead having the pressure sensor. The proximal end of the calibration vessel through which the pacing lead is inserted comprises an air tight seal between the vessel housing and the pacing lead. The distal end of the calibration vessel comprises a connector which connects the calibration vessel to either the atmosphere or an input pressure source which functions in connection with a manometer to apply an atmospheric or higher than atmospheric test pressure to the pressure sensor. Test pressure output signals of the pressure sensor under test at atmospheric pressure and under higher than or lower than atmospheric pressure are obtained. The calibration system further comprises an electronic read and display module for reading and displaying the pressure sensor output signal under atmospheric or higher than atmospheric pressure. The reference pressure output signal of an external reference pressure transducer or manometer is also provided to the electronic read and display module for comparison and calibration purposes.

When calibration shows differences between the test and reference pressure signals at sets of test pressures, the differences are encoded as one or more correction factor to be applied to the pressure signal generated by the lead borne pressure sensor under test when it is coupled with an amplifier within the IPG or implantable monitor that the lead is intended to be implanted with. The correction factors are then programmed into memory of the IPG or IHM using an external programmer and the downlink telemetry capability of the IPG or implantable monitor. In one embodiment, the lead pressure sensor is tested while attached to the electronic read and display module to determine the correction factors. In another embodiment, the terminals of the lead under test are attached to the IPG or IHM intended to be implanted in the patient. The interrogation and uplink telemetry capability of the IPG or IHM is employed with an external programmer for commanding that pressure readings at atmospheric and higher than atmospheric test pressures be taken and uplink telemetered and for receiving and displaying the uplink telemetered pressure signals. The uplink telemetered pressure readings are compared with reference pressure readings, and the correction factors are determined and downlink telemetered to the IPG or IHM.

In these tests, it is necessary to break the sterile packaging of the lead and the IPG or IHM to make the necessary electrical connections for the above described testing and calibration. Moreover, it is necessary to provide a particular pressure calibration vessel surrounding the distal portion of the lead including the pressure sensor.

Other functional tests of the IPG or implantable monitor and leads are also conducted prior to or during implantation of various implantable medical devices. For example, stimulation pulse output energies, lead conductor and electrode integrity, sensing thresholds, capture tests and the like are often conducted. A pacing system analyzer is described in U.S. Pat. No. 4,705,042 wherein the pacemaker IPG to be implanted is retained in its sterile package and coupled, along with the implanted pacing lead to the analyzer system. Sterile package connector systems for pacemaker IPGs enabling connection with a pacing system analyzer is also shown in U.S. Pat. Nos. 4,423,732 and 4,605,007.

It would be desirable to conduct tests of the types described above of IMDs employing separately sterile packaged leads and IPGs or implantable monitors adapted to be coupled together when implanted, while they remain in their sterile packages.

SUMMARY OF THE INVENTION

To this end, applicant's invention is directed to apparatus, systems and methods for coupling components of an implantable medical device that are contained within separate sterile packages together and testing functions, characteristics and operations thereof prior to chronic implantation.

In particular, the invention provides improved testing of the integrity of electrical components of a lead and the accuracy of a physiologic sensor borne by the lead while the lead is maintained within a lead sterile package and is coupled to an IPG or IHM within an IPG/IHM sterile package. The lead and IPG/IHM sterile packages need not be opened while the testing is conducted. The programmable capabilities of the IPG or IHM are employed in conjunction with an external programmer for making the tests and displaying the results to the operator of the programmer. The testing and calibration of an implantable physiologic sensor of a lead coupled to a programmable IHM or IPG while they remain in their respective sterile packages is advantageously enabled. Correction factors are derived from the testing and calibration of the sensor and are programmed into memory of the IPG/IHM for use in correcting readings made by the physiologic sensor.

The lead and IPG/IHM sterile packages are provided with package connectors that couple the terminals of the IPG/IHM and lead to external package connector arrays. The package connector arrays are coupled together, and the programmer is employed to downlink telemeter commands to the IPG or IMM to test the sensor and/or lead conductors and uplink telemeter the results to the programmer for display. When a lead borne pressure sensor is under test, the uplink telemetered pressure readings are compared to a reference pressure reading. A correction factor is determined if the uplink telemetered and reference pressure readings differ, and the correction factor is downlink telemetered from the programmer into memory of the IPG or IHM for use in adjusting the sensor pressure readings. The pressure test may be conducted both at atmospheric pressure and at elevated pressures correlated to typical systolic blood pressures, and the correction factor may be derived from all tests. Similar testing, calibration, and derivation and storage of correction factors for other types of physiologic sensors, e.g., temperature sensors, may be conducted in accordance with the present invention.

Applicant's invention provides simple but reliable lead conductor testing and testing and calibration of physiologic sensors to insure that functions performed by the IPG or IHM are based upon true readings. Applicant's invention also provides the physician with confidence that sufficient care has been taken to accurately calibrate the sensor of the pacing lead in a sterile environment. The use of the invention thus minimizes any need to replace or reprogram the implanted IPG or IHM to account for an inaccurate sensor, much to the benefit of the patient.

Applicant's invention allows the final zeroing/verification of the pressure sensor to be performed before the actual implantation procedure. Normally, a non-sterile zeroing/verification test would need to be performed as a part of the implant procedure, extending the time of the procedure, with the inherent increase in risk of infection to the patient or contamination of the IMD. The final zeroing/verification of the pressure sensor within its sterile package could even be performed days in advance of the actual implantation procedure, allowing time for a new system to be obtained for the patient if a problem is found. The Applicant's invention also allows factory testing after sterilization of the lead sterile package. This is advantageous if the physiologic sensor or transducer performance is sensitive to the sterilization pressures or gasses employed, as may be the case with a chemical sensor for sensing blood gases, blood composition, pH, and the like.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein:

FIG. 5 is a schematic exploded view of the contents of the sterile package containing the lead of FIGS. 1 and 2 depicting the proximal end of a temporary lead package connector for making an electrical connection with external electrical terminals of the lead package;

DETAILED DESCRIPTION OF THE PREFERRED EMBODIMENTS OF THE INVENTION

Applicant's invention provides apparatus, systems and methods for testing functional performance of components of IMDs while assembled together but remaining in separate sterile packages, which represents improvements over prior apparatus, systems and methods wherein at least one component was removed from its sterile package. The invention is particularly adapted to testing the functional performance of leads bearing electrodes and/or sensors adapted to be coupled with an IPG or implantable monitor, e.g., an IHM of the type described above. For purposes of illustration, the apparatus, systems and methods of the present invention are described as follows in the context of testing lead conductors and the pressure sensor of a pressure sensor bearing lead adapted to be implanted into a patient's heart and coupled with a pacemaker or ICD IPG or an IHM.

Figure 1:
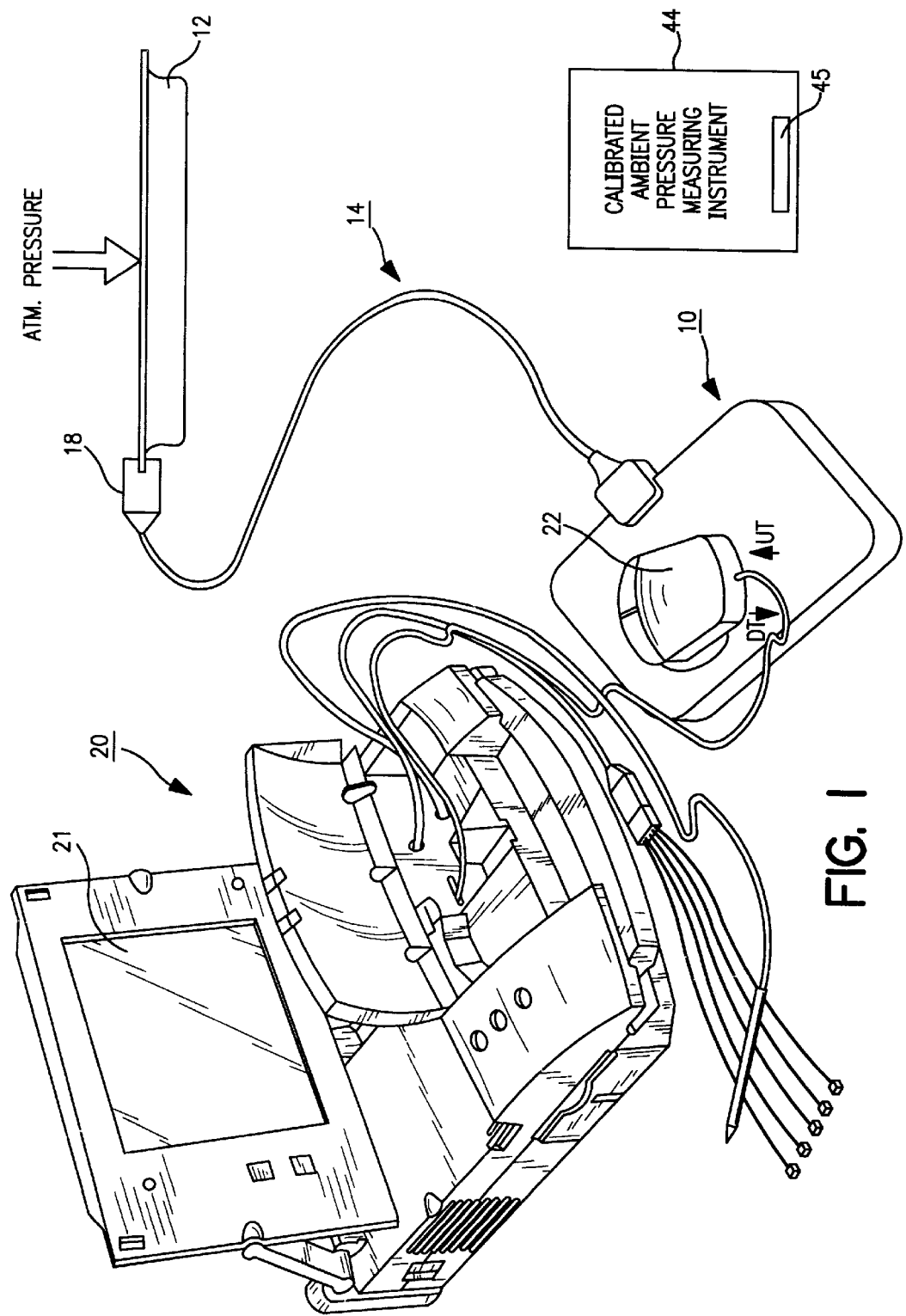
FIG. 1 is a simplified schematic view of the assembly of an IPG or IHM within a sterile package with an implantable lead within a sterile package employing a cable and the testing of the lead at atmospheric pressure employing a programmer.
Figure 2:
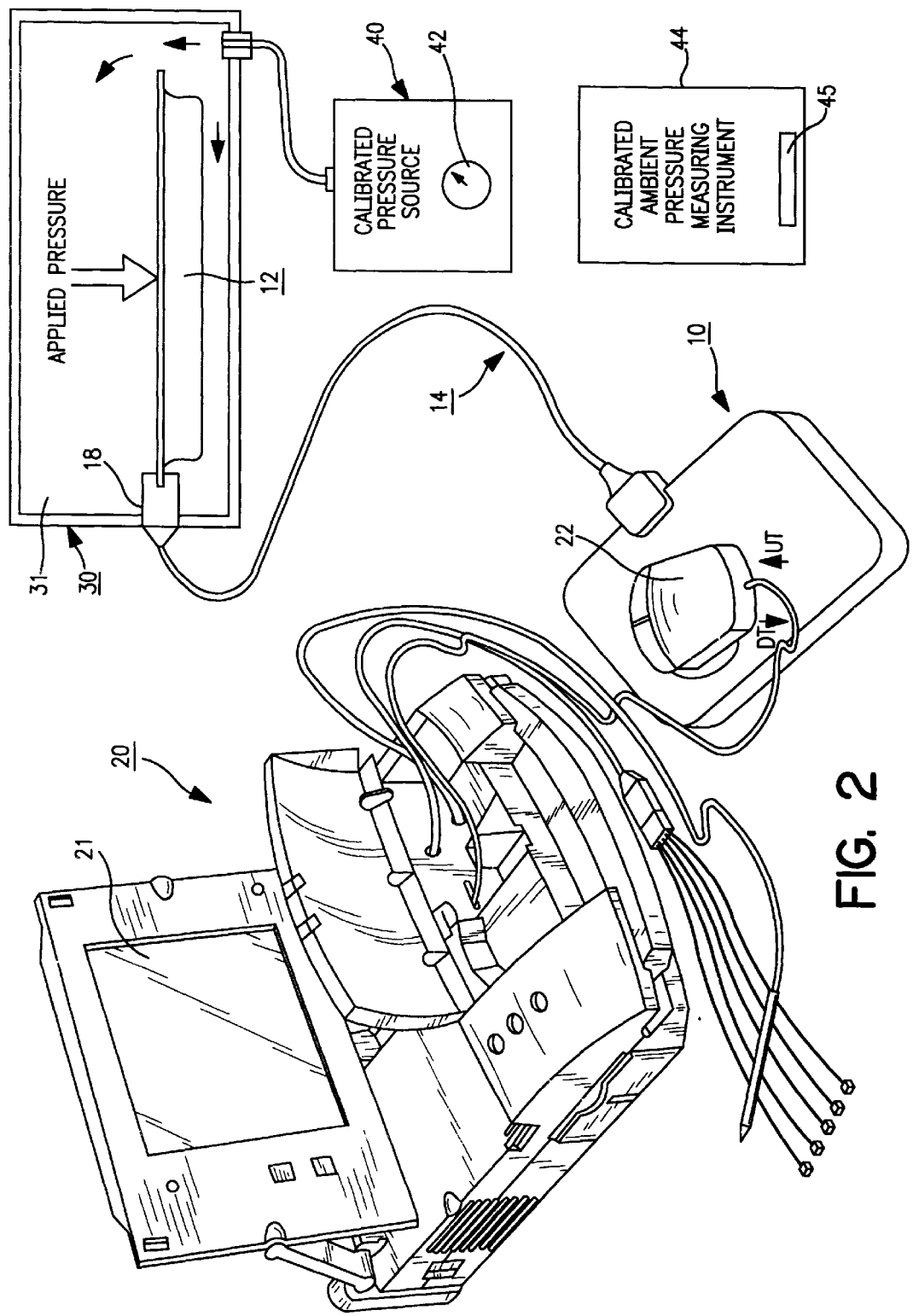
FIG. 2 is a simplified schematic view of the assembly of an IPG or IHM within a sterile package with an implantable lead within a sterile package employing a cable and the testing of the lead at higher than atmospheric pressure employing a pressure chamber and a programmer.

Thus, FIGS. 1 and 2 depict an IPG/IHM sterile package 10 holding either such an IPG or IHM coupled with an implantable lead within a lead sterile package 12 employing a connector, e.g. cable 14, coupled at a first cable connector 16 to exposed electrical terminals of the IPG/IHM sterile package 10 and at a second cable connector 18 to exposed electrical terminals of the lead sterile package 12 as described in detail below. The testing of the lead within the lead sterile package 12 is effected using programmable functions of the IPG or IHM and employing a programmer 20. The programmer 20 is preferably a MEDTRONIC® Model 9790 programmer and communicates with the IPG or IHM within the IPG/IHM package through a telemetry link between telemetry antennae in a programming head 22 and within the IPG or IHM in a manner well known in the art and as described in the above-referenced '221 patent.

A great many telemetry schemes have been employed and proposed by the assignee, Medtronic, Inc., and others for communications between IMDs and external monitors or programmers. The Model 9790 programmer 20 communicates with the IPG or IHM in IPG/IHM sterile package 10 through short range telemetry transmissions employing a 175 KHz RF carrier and close physical coupling of magnetic fields encompassing the RF telemetry antennae of the IPG or IHM and the programming head 22. Other telemetry systems have been proposed to achieve longer range, yet secure, RF telemetry between implantable and external monitors/programmers as described, for example, in commonly assigned U.S. Pat. No. 5,861,019. Such long range RF telemetry systems preferably operates at a long range of about 2 meters or more in a relatively high frequency range.

For convenience of description, the preferred embodiment is described as follows using short range RF downlink telemetry (DT) and uplink telemetry (UT) transmission, but the invention and following claims are not be interpreted as so limited. Similarly, the terms "telemeter", "telemetry transmission" and the like are intended to embrace any such action and manner of communicating and conveying data and commands between the IPG or IHM in IPG/IHM sterile package 10 and any external monitoring device or programmer 20 in the UT direction and the DT direction.

It will also be understood that the communications to and from the IPG or IHM that are employed in the practice of the present invention may take other forms than use of such short range and long range telemetry systems. The programmer 20 and the RF telemetry circuitry and functions of the IPG or IHM can be replaced by or comprise other devices to effect communications in both the UT and DT directions shown in FIGS. 1 and 2, e.g., those disclosed in commonly assigned U.S. Pat. Nos. 5,080,096 and 5,891,180. The '180 patent discloses a simplified programming scheme employing use of an externally applied magnet and an audible communication system for communicating human understandable sounds or voiced messages to the human operator. The '096 patent discloses use of a direct feed through electrical connection that can be accessed from the header of the IPG or IHM to memory within it for effecting data retrieval and programming functions. In the present case it would be possible to provide a direct electrical connection from the access point of the header of the IPG or IHM disclosed in the '096 patent with an external connector pad on the IPG/IHM sterile package in the manner for providing the package connector arrays described below.

At the outset of any test, it is first determined whether all electrical connections effected between the connector terminals of the IPG or IHM within IPG/IHM sterile package 10 and the lead connector terminals within lead sterile package 12, described in detail below, are within appropriate resistance ranges. It is necessary to make certain that the electrical connections are secure to avoid trying to test the IMD components under faulty connection conditions and reaching a faulty determination that the components are defective.

The IPG or IHM within the IPG/IHM sterile package 10 is capable of being programmed to initiate lead function tests and to uplink telemeter the resulting test data to the external programmer 20. A number of functional tests of leads are capable of being performed in modern pacemaker and ICD IPGs and IHMs. Moreover, such pacemaker and ICD IPGs and IHMs that are adapted to employ pressure sensing leads are capable of being programmed to employ downlink telemetered pressure correction factors to adjust pressure readings that are made by the pressure sensor of the pressure sensing lead that it is coupled with to ensure that device operations are based upon true pressure readings.

For example, the system of FIG. 1 may be employed in an impedance test to detect any short circuit failure between two or more of the lead conductors incorporated into a bipolar or multi-polar lead within the lead sterile package 12. Modern pacemaker and ICD IPGs and IHMs have the capability of automatically testing a variety of lead open circuit and short circuit conditions when implanted into the body and in contact with body fluids, e.g., into a heart chamber or vessel and in contact with blood. Such tests may be initiated by programmed-in commands, as taught, for example, by the above-referenced '042 patent when testing chronically implanted leads. The bipolar or multi-polar lead within lead sterile package 12 includes at least two exposed distal electrodes that are electrically separated from one another and are each coupled through electrical conductors within the elongated lead body to proximal connector elements as shown in FIG. 5 and described further below. Moreover, in the specifically described pressure sensing lead of FIG. 5, the lead conductors also function to transmit power from the IPG of IHM to power the pressure sensor components and to transmit pressure sensor output signals back to the IPG or IHM. Short circuit failures could occur within the lead body to cause the electrical conductors to contact one another or in electrical components of the pressure sensor. These failures can be detected using the system of FIG. 1 by operating the programmer 20 to command the IPG or IHM within IPG/IHM sterile package 10 to conduct a lead short circuit test and to transmit the results of the test in an uplink telemetry transmission back to the programmer 20 for display. Such a test can be conducted for any bipolar or multi-polar lead with or without a sensor. In this case, a lead that fails the impedance test is discarded.

In FIG. 1, the lead sterile package 12 is exposed to ambient air pressure, and the flexible and gas permeable cover of the lead sterile package allows air in the interior of the lead sterile package to reach the ambient air pressure rather easily. In FIG. 2, the lead sterile package 12 is contained within a pressure chamber cavity 31 of a pressure chamber 30 and exposed to higher than atmospheric or lower than atmospheric air pressure provided by a calibrated pressure source 40 in FIG. 2. The porosity and flexibility of the cover of the lead sterile package 12 allows its interior space to adjust to the changed air pressures within the pressure chamber cavity 31.

Using the system of FIG. 2, the pressure sensor bearing lead can be exposed to a range of gage pressures that would be expected to be encountered in blood of a patient's heart during systole and systole which would range from atmospheric to +100 mm Hg. There is a +/−20 mm Hg variation due to weather changes and a significant (potentially +/−50 mm Hg or more) variation due to local elevation changes. Due to the latter, it may be necessary to apply a vacuum to the lead sterile package 12 to test the pressure sensor reading at a less than atmospheric pressure at the site of the test which corresponds to atmospheric pressure where the patient typically resides. The pressure sensor of the lead may also have certain performance specifications at a range of applied pressures that can be tested correlated to the range of absolute atmospheric pressures of 450–900 mm Hg.

The calibrated pressure source 40 provides a calibrated applied pressure 42 within pressure chamber cavity 31. A calibrated ambient pressure measuring instrument 44 is used in both cases to provide a reference ambient air pressure 45 in the manner described in the above-referenced '221 patent. The reference ambient air pressure 45 and the pressure readings made by the pressure sensor of the lead within the lead sterile package 12 that are communicated via uplink telemetry and displayed on programmer display 21 by programmer 20 are observed by the operator conducting the test. The two pressure readings are compared and then employed in calculating a correction factor for that ambient pressure reading that is then transmitted to and stored in memory within the IPG or IHM within IPG/IHM sterile package 10 in a downlink telemetry transmission from programmer 20. Or the programmer 20 may be adapted as described in the above-referenced '221 patent to directly receive the reference ambient pressure from calibrated ambient pressure sensing instrument 44. In this case, an algorithm of the programmer is invoked to compare the pressure readings, calculate the correction factor, and transmit it to the IPG or IHM within IPG/IHM sterile package 10 in a downlink telemetry transmission while displaying the data and its actions to the operator.

The system of FIG. 2 is operated in a similar fashion to derive one or more correction factor for higher than atmospheric pressure readings of the pressure sensor of the lead within the lead sterile package 12 located inside a pressure chamber cavity 31 of a pressure chamber 30. The cable connector 18 is fitted into the pressure chamber wall or a the cable body of cable 14 extends through the pressure chamber wall, locating the entire cable connector 18 within the pressure chamber cavity 31 of the pressure chamber 30.

In use, the ambient air pressure correction factor is derived as described above with the pressure chamber 30 open to atmospheric pressure and the lead sterile package coupled with cable connector 18. The pressure chamber 30 is then closed, the pressure chamber cavity 31 is pressurized to the selected higher than atmospheric air pressure provided by calibrated pressure source 40 that would be expected to be encountered in operation within the human body, e.g., a systolic blood pressure. A suitable time period is allowed to pass to ensure that the interior of the lead sterile package has acclimated to the pressure change. A pressure reading of the pressure sensor are taken using the programmer 20 and compared to the applied pressure 42 at each selected elevated pressure. Then, the steps described above are followed to calculate and program a correction factor for the particular test pressure or set of correction factors to be used by the IPG or IHM when implanted with the tested pressure sensing lead.

The correction factors are associated with a measured pressure value or range of measured values and then applied by the IPG or IHM operating system to the measured pressure value. After implantation of an IHM coupled with the tested pressure sensing lead in a patient's body, the IHM periodically measures, corrects using the appropriate correction factor, and stores the corrected blood pressure values for uplink telemetry to the programmer 20, or it is commanded to make and uplink corrected blood pressure values to the programmer 20 in real time. The corrected relative physiologic signal values are also employed in therapy delivery algorithms of a pacemaker or ICD IPG to control the delivery of the therapy.

Figure 3:
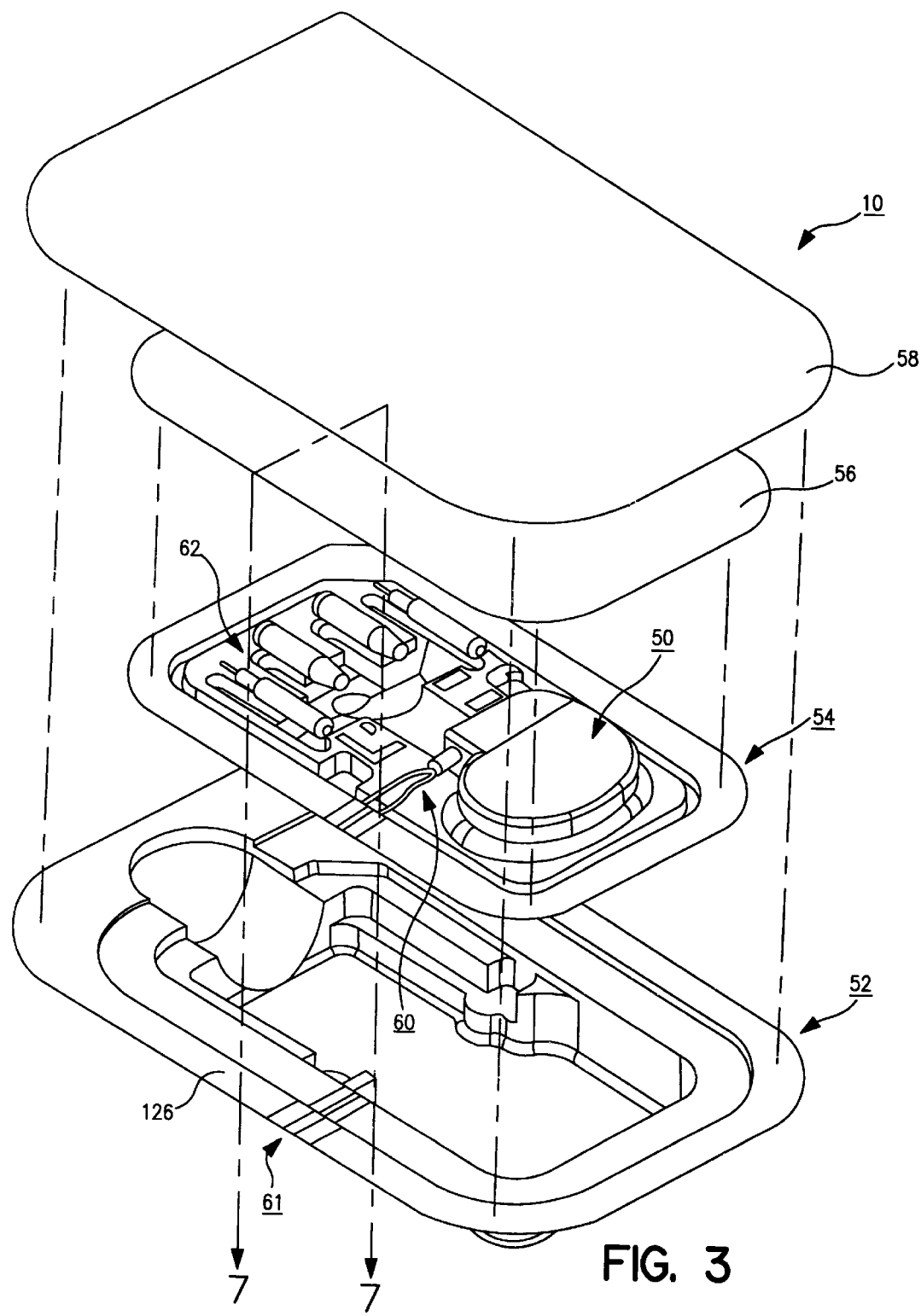
FIG. 3 is an exploded view of the sterile package containing the IPG or IHM of FIGS. 1 and 2 depicting the coupling of the connector elements of the IPG or IHM with external electrical terminals of the sterile package using a temporary IPG/IHM package connector.

FIG. 3 shows the components of the sterile package 10 of FIGS. 1 and 2 containing the IPG/IHM 50 and depicting the coupling of the connector elements of the IPG/IHM 50 with external electrical terminal array 61 of the IPG/IHM sterile package 10 using a temporary IPG/IHM package connector 60. An implantation tool set 62 for coupling a lead to the IPG/IHM 50 are also included within the IPG/IHM sterile package 10. The IPG/IHM sterile package 10 comprises a relatively rigid outer tray 52 and inner tray 54 molded in shape to accommodate the implantation tools 62 and IPG/IHM 50. An inner sheet cover 56 is fitted over and adhered to an inner tray flange 122 of the inner tray 54, and the assembly of the implantation tools 62 and IPG/IHM 50 within inner tray 54 and enclosed by inner sheet cover 56 is nested into an inner flange portion 124 of an outer tray flange 120. Then, the outer sheet cover 58 is adhered to an outer flange portion 126 of outer tray flange 120. The IPG or IHM 50, the IPG/IHM package connector 60 and the tool set 62 are thereby enclosed within a sterile chamber of the IPG/IHM package 10.

The inner and outer trays 54 and 52 are typically molded of a plastic that maintains package shape and protects the contents. The inner and outer sheet covers 56 and 58 are typically formed of Tyvek sheet material that is gas porous and allows gas sterilization of the interior of the IPG/IHM sterile package 10 after it is assembled as described above but does not allow germs and other micro-organisms to pass through it.

Figure 4:
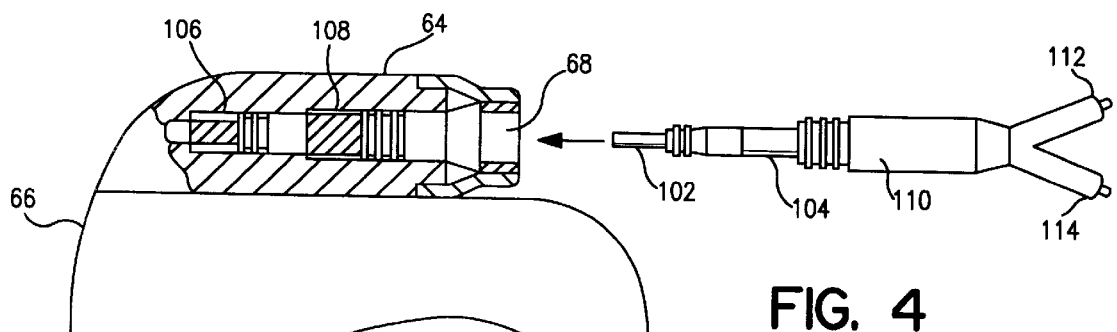
FIG. 4 is a detailed, partial, exploded view of the coupling of the proximal end of the temporary IPG/IHM package connector with the IPG or IHM connector elements.

FIG. 4 shows the coupling of the connector end 100 of the temporary IPG/IHM package connector 60 with IPG/IHM in-line connector elements contained within an in-line connector, header receptacle 68 of an electrically insulating header 64. The IPG/IHM 50 typically comprises a hermetically sealed housing 66 attached to the header 64 enclosing the battery power source, electronic circuits, memory, telemetry antenna and other components for performing monitoring, therapy delivery and telemetry functions. When implanted, the proximal lead connector end 72 of the elongated lead body 74 of lead 70 of FIG. 5 is fitted into the in-line connector, header receptacle 68 of header 64. Electrical and mechanical connection is made within header receptacle 68 between lead connector elements and header connector elements that are electrically connected with the circuits within the housing 66 by electrical feed throughs in a manner well known in the art. The particular depicted configurations of the header 64 and the proximal lead connector end 72 and the IPG/IHM package connector 60 are merely exemplary of any number of possible configurations.

FIG. 5 schematically depicts the lead sterile package 12 containing the pressure sensing lead 70 and a lead package connector 90 which receives the bipolar, in-line, proximal lead connector end 72 of the pressure sensing lead. The lead package connector 90 electrically connects the lead connector pin 82 and lead connector ring 84 to conductors 96 and 98 which are electrically connected with a schematically depicted lead package connector array 100. The lead package connector 90 includes a temporary lead connector 92 that preferably takes the form of any of those disclosed in commonly assigned U.S. Pat. No. 5,931,861 which allow a stylet (not shown) to be inserted through or removed the lumen of the lead body 74. The exemplary depicted temporary lead connector 92 has a lateral side opening 93 to receive the proximal lead connector end 72 and a rotatable clip 95 to lock the proximal lead connector end 72 within the lateral side opening 93 with the lead connector pin 82 and ring 84 received in connector clips coupled to conductors 96 and 98.

The pressure sensing lead 70 preferably takes the form disclosed in the above-referenced '752, '434, and '221 patents. The pressure sensing lead 70 includes the elongated lead body 74 enclosing two lead conductors extending to pressure sensing module 80. One lead conductor is coupled to the conductive housing of the pressure sensing module 80 which can function as an indifferent pace/sense electrode. The other lead conductor is coupled with internal electrical components of the pressure sensing module 80 and through the lead extension 78 to the active, distal pace/sense electrode 76. The manner in which the pressure sensing lead 70 and the circuitry within the IPG/IMD 50 usable with the pressure sensing lead 70 are constructed and operate is set forth in detail in the above-referenced '752 and '434 patents.

Returning to FIG. 4, the connector end 100 of the IPG/IHM package connector 60 takes the same form as the bipolar, in-line, proximal lead connector 72 of FIG. 5, and both are adapted to be received within the header receptacle 68 to make electrical connections with the header connector elements 106 and 108. The connector pin 102 and ring 104 of IPG/IHM package connector 60 are coupled with insulated conductors 112 and 114 which branch from connector body 110 and are coupled to the IPG/IHM package connector array 61.

Figures 6A, 6B:
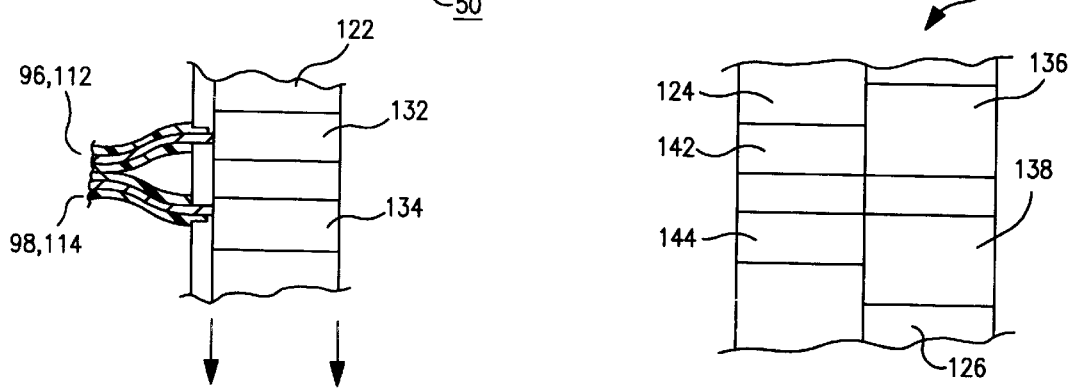
FIG. 6A is a detailed view of the coupling of the distal ends of the temporary IPG/IHM package connector or the temporary lead package connector with electrically conductive regions of the flange of an inner tray of the IPG/IHM sterile package or the lead sterile package.
FIG. 6B is a detailed view of the pattern of electrically conductive regions of the flange of the outer tray of the IPG/IHM sterile package or the lead sterile package adapted to receive the inner tray flange, make electrical connection with the inner tray conductive regions, and provide exposed electrically conductive terminals to facilitate electrical attachment of the IPG/IHM sterile package and the lead sterile package through the cable of FIG. 1.
Figures 7, 8:
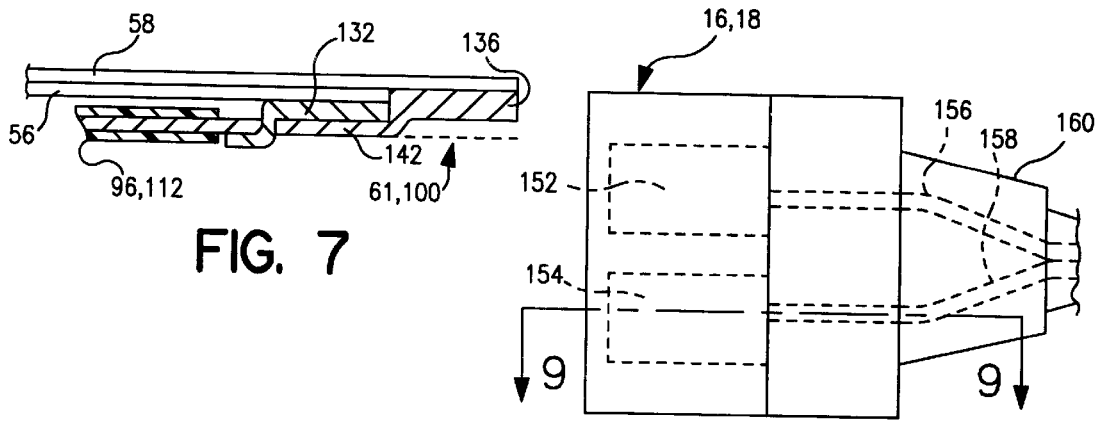
FIG. 7 is a cross-section view taken along lines 7—7 of FIG. 3 showing the package layers assembled together and including the external electrical terminals of the IPG/IHM.
FIG. 8 is a top view of a female connector of the cable of FIG. 1 and the cable and pressure chamber of FIG. 2 adapted to engage the exposed electrically conductive terminals of the IPG/IHM sterile package and the lead sterile package.

The formation of the package connector arrays 61 and 100 and the connections of the conductors 112, 114 and 96, 98 thereto are depicted in FIGS. 6A, 6B and 7. The conductor pairs 112 and 114 and 96 and 98 are connected to conductive sections 132 and 134 of the inner tray flange 122 using a conductive adhesive or solder as shown in FIG. 6A. The conductive sections 132 and 134 are mated against conductive sections 142 and 144, respectively, of outer tray inner flange 124 which are continuously fabricated with conductive sections 136 and 138, respectively, of outer tray outer flange 126 as shown in FIGS. 6B and 7. The conductive sections of the inner and outer tray flanges can be formed by electrically conductive film coatings and/or adhesive layers and/or powder or particulate materials of conductive wires embedded into the plastic that the inner and outer trays are formed of. Conductive adhesives or thermal and pressure bonding may be employed to bond the conductive portions 132 and 142 together and 134 and 144 together.

Figure 9:
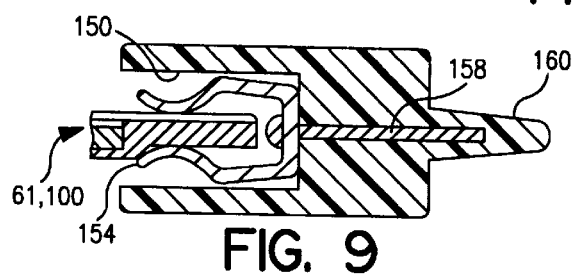
FIG. 9 is a cross-section view along lines 9—9 of FIG. 8 depicting the mechanical and electrical connection of the male electrically conductive terminals of the IPG/IHM sterile package and the lead sterile package with the female connector of FIG. 8.

The resulting sandwich layers of the package connector arrays 61, 100 are depicted in cross-section in FIG. 7. The lower surfaces of the outer flange portion 126 at conductive portions 136 and 138 are conductive, and cable connectors 16 and 18 can be coupled therewith without disturbing the cover sheet 58 adhered to the upper surface thereof as shown in FIGS. 8 and 9. The lower surfaces of the outer flange portion 126 on either side of conductive portions 136 and 138 could be made thicker as shown in broken lines to facilitate positioning of the cable connectors 16, 18 with the package connector arrays 61, 100.

FIGS. 8 and 9 depict the attachment of the cable connectors 16, 18 with the package connector arrays 61, 100. The clip connectors 152, 154 within U-shaped channel 150 engage the lower surface of conductive portions 136 and 138 and are electrically connected with cable conductors 156 and 158 embedded within cable body 160.

The form and construction of the cable 14, IPG/IHM package connector 60 and lead package connector 90, the cable connectors 16, 18, and the package connector arrays 61, 100 may be widely varied. The package connector arrays 61, 100 may alternatively take any of the forms disclosed in the above-referenced '042, '732 and '007 patents, for example, and the cable connectors 16, 18 may be configured to be attached to them.

For example, the cable 14 and connectors 16 and 18 could be replaced by a much shorter, single piece element incorporating the connectors 16 and 18 and the conductors extending between them into a single housing. Or a female connector like cable connector 16, 18 shown in FIGS. 8 and 9 could be incorporated into one of the IPG/IHM or lead sterile packages 10 or 12 in substitution for the package connector array 61 or 100, so that the IPG/IHM and lead sterile packages 10 and 12 could be directly coupled together.

Thus, the above-described apparatus, systems and methods couple components of an implantable medical device that are contained within separate sterile packages together testing functions, characteristics and operations thereof prior to chronic implantation. In particular, the testing of lead conductor integrity and the testing and calibration of an implantable pressure sensor, coupled to a programmable, implantable hemodynamic monitor (IHM) or implantable pulse generator (IPG) while in respective sterile packages are disclosed. It will be understood that other physiologic sensors may be tested in a similar manner. For example, the pressure sensor 80 can also provide a temperature reading at room temperature and at body temperature (if the lead sterile package is placed within a calibrated oven) that can be uplink telemetered and compared to a reference temperature to derive a temperature correction factor for downlink telemetry and storage in memory in the IPG or IHM.

The above-described testing of the physiologic sensor assumes that the sensor readings can be corrected by application of a correction factor to the sensor readings to provide true sensor readings. The true sensor readings can be employed to determine if a therapy is to be delivered, e.g., a cardioversion/defibrillation shock, and/or to adjust the parameters of a delivered therapy, e.g., pacing rate, and/or can be stored in IPG/IHM memory for later uplink telemetry to the programmer. But, it will be understood that the test procedure of the present invention can also be employed to determine that a defective physiologic sensor is not functional or does not provide sensor readings that can be corrected to provide true sensor readings, in which case the lead may be discarded or returned to its manufacturer without opening the lead sterile package and possibly voiding a warranty.

The preceding specific embodiments are therefore to be understood as illustrative of the many ways in which the principles of the invention may be practiced. It is to be understood, therefore, that other expedients known to those of skill in the art or disclosed herein may be employed without departing from the invention or the scope of the appended claims.

It is therefore to be understood, that within the scope of the appended claims, the invention may be practiced otherwise than as specifically described without actually departing from the spirit and scope of the present invention.

What is claimed is:

1. A method of coupling first and second components of an implantable medical device that are contained within separate sterile packages together and testing functions, characteristics and operations thereof prior to chronic implantation comprising:

providing a first component sterile package having a first component sterile package connector array on an external surface thereof;

placing the first component having first component terminals in the first component sterile package;

coupling the first component terminals with the first component sterile package connector array through a first component sterile package connector;

enclosing the first component and first component sterile package connector coupled therewith within the first component sterile package;

providing a second component sterile package having a second component sterile package connector array on an external surface thereof;

placing the second component having second component terminals in the second component sterile package;

coupling the second component terminals with the second component sterile package connector array through a second component sterile package connector;

enclosing the second component and second component sterile package connector coupled therewith within the second component sterile package;

coupling the first component sterile package connector array with the second component sterile package connector array to assemble the first and second components in as the operative implantable medical device; and testing at least one of the functions, characteristics and operations of the implantable medical device.

2. The method of claim 1, wherein the first component comprises an implantable monitor or therapy delivery device and the second component further comprises an elongated lead having lead conductors formed therein coupled with electrical lead components, and the testing method further comprises:

operating the implantable monitor or therapy delivery device to effect a test of the integrity of the lead conductors and electrical lead components coupled therewith; and communicating the results of the test from the implantable monitor or therapy delivery device to enable determination if lead integrity criteria are achieved.

3. The method of claim 1, wherein the first component comprises an implantable monitor or therapy delivery device and the second component further comprises a physiologic sensor that provides a sensor reading of a physiologic condition of a patient when implanted in the patient, and the testing method further comprises:

operating the implantable monitor or therapy delivery device to obtain a sensor reading from the physiologic sensor;

providing a reference sensor reading; and communicating the sensor reading from the implantable monitor or therapy delivery device to enable comparison of the reading from the physiologic sensor to the reference sensor reading.

4. The method of claim 3, wherein the physiologic sensor comprises an implantable blood pressure sensor, and wherein:

the reference sensor reading providing method comprises obtaining an atmospheric pressure reading taken by a calibrated ambient pressure measuring instrument; and the operating method further comprises the step of exposing the pressure sensor to atmospheric pressure applied through the second component sterile package while obtaining the sensor reading.

5. The method of claim 3, wherein the physiologic sensor comprises an implantable blood pressure sensor, and wherein:

the operating method further comprises the step of exposing the pressure sensor to a pressure applied through the second component sterile package and correlated with a blood pressure of a patient while obtaining the sensor reading; and the reference sensor reading providing step comprises measuring the applied pressure with a calibrated applied pressure measuring instrument.

6. The method of claim 1, wherein the first component comprises a remotely programmable, implantable monitor or therapy delivery device and the second component comprises a physiologic sensor that provides a sensor reading of a physiologic condition of a patient when implanted in the patient, and the testing method further comprises:

programming the implantable monitor or therapy delivery device to obtain a sensor reading from the physiologic sensor;

providing a reference sensor reading;

communicating the sensor reading from the implantable monitor or therapy delivery device to a remote programmer;

comparing the reading from the physiologic sensor to the reference sensor reading to determine if they differ;

determining a correction factor from any determined difference between the reference and physiologic sensor readings; and programming the implantable monitor or therapy delivery device to employ the correction factor to adjust a sensor reading obtained from the physiologic sensor to a true sensor reading.

7. The method of claim 6, wherein the physiologic sensor comprises an implantable blood pressure sensor, and wherein:

the reference sensor reading providing method comprises obtaining an atmospheric pressure reading taken by a calibrated ambient pressure measuring instrument; and the operating step further comprises the method of exposing the pressure sensor to atmospheric pressure applied through the second component sterile package while obtaining the sensor reading.

8. The method of claim 6, wherein the physiologic sensor comprises an implantable blood pressure sensor, and wherein:

the operating method further comprises the step of exposing the pressure sensor to a pressure applied through the second component sterile package and correlated with a blood pressure of a patient while obtaining the sensor reading; and the reference sensor reading providing method comprises measuring the applied pressure with a calibrated applied pressure measuring instrument.

9. A system for coupling first and second components of an implantable medical device that are contained within separate sterile packages together and testing functions, characteristics and operations thereof prior to chronic implantation comprising:

a first component sterile package containing the first component within a first sterile chamber and having a first component sterile package connector array on an external surface thereof;

a first component sterile package connector within the first sterile chamber coupled between electrical terminals of the first component and the first component sterile package connector array;

a second component sterile package containing the second component within a second sterile chamber and having a second component sterile package connector array on an external surface thereof;

a second component sterile package connector within the second sterile chamber coupled between electrical terminals of the second component and the second component sterile package connector array;

a cable to couple the first component sterile package connector array with the second component sterile package connector array to assemble the first and second components in as the operative implantable medical device; and means for testing at least one of the functions, characteristics and operations of the implantable medical device.

10. The system of claim 9, wherein:

the first component comprises an implantable monitor or therapy delivery device;

the second component further comprises an elongated lead having lead conductors formed therein coupled with electrical lead components; and the testing means further comprises:

means for operating the implantable monitor or therapy delivery device to effect a test of the integrity of the lead conductors and electrical lead components coupled therewith; and means for communicating the results of the test from the implantable monitor or therapy delivery device to enable determination if lead integrity criteria are achieved.

11. The system of claim 9, wherein the first component comprises an implantable monitor or therapy delivery device within the first component sterile package;

the second component further comprises a physiologic sensor within the second component sterile package that provides a sensor reading of a physiologic condition of a patient when implanted in the patient; and the testing means further comprises:

means for operating the implantable monitor or therapy delivery device to obtain a sensor reading from the physiologic sensor;

means for providing a reference sensor reading; and means for communicating the sensor reading from the implantable monitor or therapy delivery device to enable comparison of the reading from the physiologic sensor to the reference sensor reading.

12. The system of claim 11, wherein the physiologic sensor comprises an implantable blood pressure sensor exposed to atmospheric pressure transmitted through the second component sterile package; and the reference sensor reading providing means comprises a calibrated ambient pressure measuring instrument that provides a reference atmospheric pressure reading.

13. The system of claim 11, further comprising:

a pressure chamber having a pressure chamber cavity in which the second component sterile package is located; and wherein:

the physiologic sensor comprises an implantable blood pressure sensor exposed to pressure transmitted through the second component sterile package;

the operating means further comprises means for applying a pressure correlated with a blood pressure of a patient to the pressure chamber cavity to expose the pressure sensor to the applied pressure transmitted through the second component sterile package; and the reference sensor reading providing means comprises a calibrated applied pressure measuring instrument measuring the applied pressure within the pressure chamber cavity.

14. The system of claim 9, wherein the first component comprises a remotely programmable, implantable monitor or therapy delivery device;

the second component comprises a physiologic sensor that provides a sensor reading of a physiologic condition of a patient when implanted in the patient; and the testing means further comprises:

means for providing a reference sensor reading;

a programmer to program the implantable monitor or therapy delivery device to obtain a sensor reading from the physiologic sensor, to communicate the sensor reading from the implantable monitor or therapy delivery device to the programmer, and to program the implantable monitor or therapy delivery device to employ a correction factor to adjust a sensor reading obtained from the physiologic sensor to a true sensor reading, wherein the correction factor is determined from any difference between the reference and physiologic sensor readings.

15. The system of claim 14, wherein
the physiologic sensor comprises an implantable blood pressure sensor exposed to atmospheric pressure transmitted through the second component sterile package; and
the reference sensor reading providing means comprises a calibrated ambient pressure measuring instrument that provides a reference atmospheric pressure reading.

16. The system of claim 14, further comprising:
a pressure chamber having a pressure chamber cavity in which the second component sterile package is located; and wherein:
the physiologic sensor comprises an implantable blood pressure sensor exposed to pressure transmitted through the second component sterile package;
the operating means further comprises means for applying a pressure correlated with a blood pressure of a patient to the pressure chamber cavity to expose the pressure sensor to the applied pressure transmitted through the second component sterile package; and
the reference sensor reading providing means comprises a calibrated applied pressure measuring instrument measuring the applied pressure within the pressure chamber cavity.

17. Apparatus for coupling first and second components of an implantable medical device that are contained within separate sterile packages together and testing functions, characteristics and operations thereof prior to chronic implantation comprising:
a first component sterile package containing the first component within a first sterile chamber and having a first component sterile package connector array on an external surface thereof;
a first component sterile package connector within the first sterile chamber coupled between electrical terminals of the first component and the first component sterile package connector array;
a second component sterile package containing the second component within a second sterile chamber and having a second component sterile package connector array on an external surface thereof;
a second component sterile package connector within the second sterile chamber coupled between electrical terminals of the second component and the second component sterile package connector array;
means for coupling the first component sterile package connector array with the second component sterile package connector array to assemble the first and second components in as the operative implantable medical device; and
means for testing at least one of the functions, characteristics and operations of the implantable medical device.

18. The apparatus of claim 17, wherein
the first component comprises a remotely programmable, implantable monitor or therapy delivery device;
the second component comprises a physiologic sensor that provides a sensor reading of a physiologic condition of a patient when implanted in the patient; and
the testing means further comprises:
means for providing a reference sensor reading;
a programmer to program the implantable monitor or therapy delivery device to obtain a sensor reading from the physiologic sensor, to communicate the sensor reading from the implantable monitor or therapy delivery device to the programmer, and to program the implantable monitor or therapy delivery device to employ a correction factor to adjust a sensor reading obtained from the physiologic sensor to a true sensor reading, wherein the correction factor is determined from any difference between the reference and physiologic sensor readings.

19. The system of claim 18, wherein
the physiologic sensor comprises an implantable blood pressure sensor exposed to atmospheric pressure transmitted through the second component sterile package; and
the reference sensor reading providing means comprises a calibrated ambient pressure measuring instrument that provides a reference atmospheric pressure reading.

20. The apparatus of claim 17, wherein
the first component comprises an implantable monitor or therapy delivery device;
is the second component further comprises an elongated lead having lead conductors formed therein coupled with electrical lead components; and
the testing means further comprises:
means for operating the implantable monitor or therapy delivery device to effect a test of the integrity of the lead conductors and electrical lead components coupled therewith; and
means for communicating the results of the test from the implantable monitor or therapy delivery device to enable determination if lead integrity criteria are achieved.

\* \* \* \* \*

UNITED STATES PATENT AND TRADEMARK OFFICE
CERTIFICATE OF CORRECTION

PATENT NO. : 6,292,697 B1
DATED : September 18, 2001
INVENTOR(S) : Jonathan P. Roberts It is certified that error appears in the above-identified patent and that said Letters Patent is hereby corrected as shown below:

Column 16,
Line 36, delete the word "is".

Signed and Sealed this

Fourth Day of February, 2003

JAMES E. ROGAN
*Director of the United States Patent and Trademark Office*